United States Patent [19]

Volchenskova et al.

[11] Patent Number: 5,087,712

[45] Date of Patent: Feb. 11, 1992

[54] DERIVATIVES OF PLATINUM (II) WITH POLYMETHYLSILOXANE, METHOD FOR PREPARING SAME AND ANTITUMOR AGENT BASED THEREON

[76] Inventors: Ilima I. Volchenskova, ulitsa Terem kovskaya, 13, kv. 40, Kiev; Nadezhda N. Maidanevich, oblast, Kievo-Svyatoshinsky raion, Vishnevy, ulitsa Oktyabrskaya, 13, kv. 49, Kievskaya; Lev. I. Budarin, ulitsa Semashko, 10, kv. 31, Kiev; Inna M. Samodumova, prospekt Nauki, 103/2, kv. 44, Kiev; Vitaly N. Girin, ulitsa Florentsii, 1/11, kv. 57, Kiev, all of U.S.S.R.

[21] Appl. No.: 582,921

[22] PCT Filed: Jan. 30, 1990

[86] PCT No.: PCT/SU90/00034

§ 371 Date: Oct. 3, 1990

§ 102(e) Date: Oct. 3, 1990

[87] PCT Pub. No.: WO90/08768

PCT Pub. Date: Aug. 9, 1990

[30] Foreign Application Priority Data

Jan. 2, 1989 [SU] U.S.S.R. ............................. 4645412

[51] Int. Cl.$^5$ ............................................ C07F 15/00
[52] U.S. Cl. ......................................... 556/137; 556/9; 556/431; 514/492; 528/15
[58] Field of Search .............. 556/9, 137, 431, 443, 556/465; 514/6, 63, 492; 260/665 R; 528/14, 15

[56] References Cited

U.S. PATENT DOCUMENTS

| | | | |
|---|---|---|---|
| 4,544,759 | 10/1985 | Hlavka et al. | 556/36 |
| 4,647,679 | 3/1987 | Panster et al. | 556/9 |
| 4,847,228 | 7/1989 | Saruyama | 556/9 X |
| 4,870,062 | 9/1989 | Kurono et al. | 514/492 X |

FOREIGN PATENT DOCUMENTS

| | | |
|---|---|---|
| 0152366 | 8/1984 | European Pat. Off. |
| 0098135 | 11/1984 | European Pat. Off. |
| 0210291 | 4/1987 | European Pat. Off. |
| 3521893 | 6/1984 | Fed. Rep. of Germany |
| 1192596 | 8/1985 | U.S.S.R. |
| 8503296 | 1/1984 | World Int. Prop. O. |

OTHER PUBLICATIONS

Handbook of Cancer Combination Chemotherapy '85; Nippon Kayaku, Nov. 1986, Japanese Originals and English Originals.

*Primary Examiner*—Arthur C. Prescott
*Attorney, Agent, or Firm*—Ladas & Parry

[57] ABSTRACT

Derivatives of platinum (II) with polymethylsiloxane comprising xerogels—a product of interaction of a complex compound of platinum (II) in an aqueous solution of sodium chloride with a hydrogel of polymethylsiloxane at a molar ratio of Pt:Si:NaCl of 1-3:50:23-69 consisting a three-dimensional cross-linked polymer of a globular structure with a globule diameter of 4.0-7.0 nm and a specific surface area of 80-200 m$^2$/g having a unit of the general formula:

$$\{[PtCl(NH_3)_2O_{0.5}]_n(NaCl)_{5n}(CH_3SiO_{1.5})_{50}(Na_2O)_{10}(H_2O)_{20}\}$$

wherein n = 1 to 3.

A method for preparing said compounds comprising reacting a complex compound of platinum (II) in an aqueous solution of sodium chloride with a hydrogel or polymethylsiloxane at a molar ratio of Pt:Si:NaCl = 1-3:50:23-69, followed by isolation of the desired product.

The compounds of the invention exhibit an antitumor activity. The antitumor agent according to the present invention consists of an active principle—the compound of the present invention having a unit of the formula:

$$\{[PtCl(NH_3)_2O_{0.5}]_2(NaCl)_{10}(CH_3SiO_{1.5})_{50}(Na_2O)_{10}(H_2O)_{20}\}$$

5 Claims, No Drawings

DERIVATIVES OF PLATINUM (II) WITH POLYMETHYLSILOXANE, METHOD FOR PREPARING SAME AND ANTITUMOR AGENT BASED THEREON

FIELD OF THE ART

The present invention relates to the art of bioinorganic chemistry and, more particularly, to novel compounds—derivatives of platinum (II) with polymethylsiloxane, to a method for preparing same and to an agent of an antitumor effect based thereon.

PRIOR ART

At the present time the death rate of the population, especially of persons of a young and middle age due to malignant tumors of different location is growing everywhere. In this connection, a great attention is paid to the development and investigation of antitumor-action pharmaceutical preparations.

Among chemotherapeutic preparations employed as antitumor agents one of the most active and widely used in medicinal practice is a synthetic preparation of an inorganic nature—cis-dichlorodiammonioplatinum (II)/CDDP, Cis-platin/ (Handbook of Cancer. Combination chemotherapy'85, Bleomycin, Peplomycin, Cis-platin, Nippon Kayaku 1986, p. 6-7, 26-27, 46-47, 61-63). As an antitumor preparation CDDP is used in mono- and polychemotherapy in cases of cancer of the urogenital sphere, tumors of lungs, head, neck and central nervous system, as well as in the cases of lymphomae and in oncogenicology. The effectiveness of therapy of ovary carcinoma through administration of the preparation CDDP in combination with vinblastin, actinomycin and prednisolone is as high as 100%.

However, CDDP is a highly toxic preparation which causes injury of kidneys, vomition, giddiness, suppression of medullary hemopoiesis, disturbances of audition, allergic responses, electrolytical disorders and neurological symptoms.

The most dangerous side effect which is revealed in the therapy with the preparation CDDF is its nephrotoxicity limiting the therapeutic dose of the preparation. The disturbance of the kidneys' function is associated with the injury of glomerules and tubules and is manifested in a high level of urina, creatinine, uric acid in the biochemical blood examination parameters.

The suppression of the medullary hemopoiesis can be caused also by the dose and duration of the treatment. The preparation CDDF injures all three branches of the hemopoiesis. The appearance of leukopeniae varies from 0 to 52%, that of anemiae—from 9 to 40%. There are also cases of gemolytic anemia.

Due to the high nephro- and hematotoxicity, during the treatment with the preparation of CDDF it is necessary to regularly ccary out analyses of biochemical parameters and blood formula.

Well known in the art at the present ime are also antitumor preparations containing, as the active principle, organic substances of a synthetic or natural origin (alkylation agents, antimetabolics, antibiotics, alkaloids, enzymes, hormones and the like).

These preparations are inferior to the preparation CDDF in respect of the level of their anti-tumor effect. Furthermore, they produce a side effect on the cardiac muscle, hemopoiesis, gastro-intestinal tract. All known preparations of the anti-tumor effect suppress the immunological reactivity of the organisms to a certain extent.

DISCLOSURE OF THE INVENTION

The compounds according to the present invention, the method for preparing same and a pharmaceutical agent based thereon are novel and hitherto unknown in the literature.

The main object of the present invention is to provide novel compounds featuring a high antitumor activity in combination with a low toxicity, which would not suppress the immunological reactivity of the organism and be useful as antitumor agents for administration directly onto the tumor and adjacent tissues, as well as to provide a method for preparing said compounds.

The object of the present invention is accomplished by novel compounds, viz. derivatives of platinum (II) with polymethylsiloxane comprising xerogels—a product of interaction of a complex compound of platinum (II) in an aqueous solution of sodium chloride with a hydrogel of polymethylsiloxane at a molar of Pt:Si:-NaCl equal to 1-3:50:23-69 representing a three-dimensional cross-linked polymer of a globular structure with a globule diameter of 4.0 to 7.0 nm and having a specific surface area of 80.0-200.0 m$^2$/g with a unit of the following general formula:

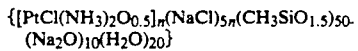

$$\{[PtCl(NH_3)_2O_{0.5}]_n(NaCl)_{5n}(CH_3SiO_{1.5})_{50}\cdot(Na_2O)_{10}(H_2O)_{20}\}$$

wherein n ranges from 1 to 3.

The compounds according to the present invention have an antitumor activity, they do not suppress the immune system and are low-toxic compounds; they also ensure the possibility of introducing platinum-containing substances directly onto the tumors and the tissues adjacent thereto and can be useful in medicine as antitumor agents.

An antitumor agent according to the present invention consists of an active principle—a derivative of platinum (II) with polymethylsiloxane having a unit of the formula:

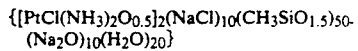

$$\{[PtCl(NH_3)_2O_{0.5}]_2(NaCl)_{10}(CH_3SiO_{1.5})_{50}\cdot(Na_2O)_{10}(H_2O)_{20}\}$$

The compound according to the present invention has a high level of an antitumor activity, a low toxicity, is does not suppress the immune system of the organism in general, stimulates a local cell immunity, ensures the possibility of a direct administration of the most active derivative of platinum (II) with polymethylsiloxane direclty onto the tumor anjd tissues adjacent thereto in chemotherapy of ovary cancer, mammal carcinoma, pancreas carcinoma, gallbladder carcinoma, cancer of large and small intestine.

The compounds according to the present invention are prepared by reacting a complex compound of platinum (II) in an aqueous solution fo sodium chloride with a hydrogel of polymethylsiloxane at a molar ratio of Pt:Si:NaCl equal to 1-3:50:23-26 respectively, followed by siolation of the desired product.

As the complex compound of platinum (II) according to the present invention it is preferable to use cis-dichlorodiamminoplatinum or sodium tetrachloriplatinite whihc, prior to its interaction with a hydrogel of polymethylsiloxane, is treated in water with ammonium acetate in a molar ratio of 1:4, respectively, at the boiling temperature with separatioan of the formed precipitate.

BEST MODE TO CARRY OUT THE INVENTION

The compounds according to the present invention comprise exerogels in the form of fine amorphous white powders of a yellowish colour of different shades, without odour, air-resistant and capable of being stored for three years without changing their properties. They have no characteristic melting point. The compounds are insoluble in organic solvents and do not swell in them, they are nonhydroscopic, non-wettable with water, but wettable with ethanol, acetone, chloroform and other organic liquids.

The compounds according to the present invention are polymeric substances. Their macromolecules have a three-dimensional chain-reticulated structure and coiled into globules of a diameter of 4.0–7.0 nm with a specific surface area of 80.0–200.0 m$^2$/g. Upon heating for 8 hours at a temperature of from 40° to 120° C. the compounds according to the present invention do not undergo any visible changes, but under heating over 120° C. they start to decompose.

The IR-spectra of the compounds according to the present invention have absorption bands within the regions of 400–700 cm$^{-1}$ (deformation vibrations of the Si—O—Si group), 780–790 cm$^{-1}$ (stretching vibrations of the Si—C group), 840–850 cm$^{-1}$ (deformation vibrations of the O—H and N—H groups), 1,040–1,140 cm$^{-1}$ (stretching vibrations of the Si—O—Si grup), 1,260–1,280 cm$^{-1}$, 1,380–1,470 cm$^{-1}$ (deformation vibrations of the C—H grup), 1,600–1,700 cm$^{-1}$ (deformation vibrations of the O—H and N—H groups), 2,800–3,000 cm$^{-1}$ (stretching vibrations of the C—H group), 3,200–4,000 cm$^{-1}$ (stretching vibrations of the N—H and O—H groups).

The compound according to the present invention whose macromolecule has a unit of the formula:

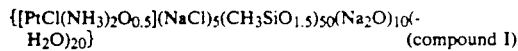 (compound I)

placed in the amount of 1.0 g into 12 ml of an aqueo-ethanolic mixture (5:1) forms a solution over the precipitate which has a pH value of 5.52 and a molar electrical conductivity $\mu = 130 \pm 7.0$ Ohm$^{-1}$.cm$^2$.mol$^{-1}$ at 20° C. as based on the content of sodium chloride.

The UF spectrum of the compound (I) suspended in 10 ml of glycerol has two absorption maximums within the region of from 200 to 400 nm at 215.5±0.2 and 295.5±0.2 nm and an optical density $E_{215.5} = 0.250$ and $E_{295.5} = 0.040$ at the thickness of the absorption layer of 1 cm.

The spectrum of reflection of the compound (I) in xtreme points has the spectral reflection coefficients $R_{260}(\%) = 47.81$, $R_{333.3}(\%) = 64.36$, $R_{401.0}(\%) = 71.26$, $R_{514}(\%) = 88.07$, $R_{836.0}(\%) = 96.17$, $R_{862.0}(\%) = 8.03$.

The amount of platinum released form 1.0 g of a powder of the compound (I) in 12 ml of a water-ethanol mixture (5:1) after one day is 18.0%, after 2.5days—29.8%. Later on, from the solid sample no platinum is passed into solution during '-3 months.

The compound according to the present invention having a unit of the formula:

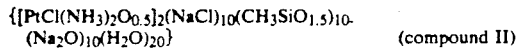 (compound II)

introduced in the amount of 1.0 g into 12 ml of a water-ethanol mixture (5:1) forms a solution over the precipitate which at 20° C. has the pH of 5.85 and the molar electrical conductivity $\mu = 128 \pm 7.0$ Ohm$^{-1}$.cm$^2$.mol$^{-1}$ (as calculated for the content of sodium chloride).

The UV-spectrum of 0.048 g of the compound (II) suspended in 10 ml of glycerol has two maximums within the range of from 200 to 400 nm at 217.9±0.2, 278.5±0.2 nm, a shoulder at 333.5±0.2 nm and the optical density $E_{217.9} = 0.490$, $E_{278.9.5} = 0.080$ and $E_{333.5} = 0.035$ at the absorption layer thickness pf 1 cm.

The reflection spectrum of the compound (II) has no extreme points.

The amount of platinum released from 1.0 g of the compound (II) in 12 ml of a water-ethanol mixture (5:1) after one day is 22.5%, after 3 days—37.0%. The remaining platinum is not released from samples for 3 months.

The compound according to the present invention having a unit of the formula:

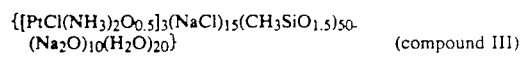 (compound III)

treated in the amount of 1.0 g with 12 ml of a water-ethanol mixture (5:1) forms a solution oer the precipitate which solution at 20° C. has the pH of 5.92 and the molar electrical conductivity $\mu = 140 \pm 7.0$ Ohm$^{-1}$. ~cm$^2$.mol$^{-1}$ as calculated for the content of sodium chloride.

The UV-spectrum of 0.048 g.of the compound (III) suspended in 10 ml of glycerol within the range of from 200 to 400 nm has two maximums at 219.1±0.2 nm and the optical density $E_{219.1} = 0.750$ and $E_{270.5} = 0.125$ at the absorption layer thickness of 1 cm.

The reflection spectrum of the compound (III) has no extreme points.

The amount of platinum released from 1.0 g of the compound (III) in 12 ml of a wter-ethanol mixture (5:1) after one day is 27.0%, after 3 days—42.0%. The remaining platinum in the sample is not released thereform for 2 months.

The compounds according to the present invention exhibit an antitumor activity in combination with promotion of the local cell immunity, as well as the ability of ensuring a direct administration of a derivative of platinum (II) onto the tumor and tissues adjacent thereto. The compound according to the present invention and the antitumor agent baswed thereon have been experimentally tested on animals and in clinics of human patients.

Their antitumor activity was studies in respect of regrafted Schvetz's erythroleukosis. The antitumor activity of each of the compounds according to the present invention was assessed from the experiments carried out on white non-descript rats with a mass of 150–200 g (10 animals in a group). The animals were hypodermally inoculated (in the thigh) with 2×10$^8$ cells of a regrafted Schvetz's erythroleukosis strain. On the 4th day after inoculation of the tumor cells, i.e. during the period of the lograithmic phase of the tumor growth the animals were administered with the compounds according to the present invention. They were administered once intraperitoneally or directly into the tumor node as powders. The compounds according to the present invention were administered in maximum effective and minimum effective doses:

| Maximum ED, mg/kg | | Minimum ED, mg/kg | |
|---|---|---|---|
| compound I | 2,400 | compound I | 506 |
| compound II | 1,100 | compound II | 180 |
| compound III | 600 | compound III | 150 |

The antitumor effect of the compounds according to the present invention was studies in comparison with the control and with the known preparations—CDDP and polymethylsiloxane.

The administered dose of CDDF was 8.1 mg/kg, that of polymethylsiloxane—4,000 mg/kg. CDDP was introduced in the form of 3 ml of a solution containing 0.015 mol/l of NaCl and 0.0015 mol/l of sodium citrate. Polymethylsiloxane was introduced in the form of a powder. Prior to administration the powders of polymethylsiloxane and of the compounds according to the present invention were sterilized by autoclaving in sealed flasks or in package from parchment paper for one hour under the excessive pressure of 1.0 atm and at the temperatuer of 100° C.

The animals were narcotized by way of a hypodermal injection of hexenal in a dose of from 40 to 60 mg/kg in the case of an intraperitoneal adminsitration of the compounds according to the present invention. After 30-60 minutes after injection of the narcotic the animals were immobilized, their abdominal cavity was opened, sterile powders of polymethylsiloxane and the compounds according to the present invention were introduced thereinto in the above-specified doses distributing them with maximum uniformity, whereafter the wound was sewn by a purse-string suture. After discontinuation of the effect of hexenal the animals were awakened.

In the case of administration of polymethylsiloxane and the compounds according to the present invention directly into the tumor, the animals were narcotized in a similar manner, then they were immobilized, the skin of the thigh was dissected along the underlying tissues, the latter were separated from the tumor node and the test compounds were introduced into the formed cavity and directly onto the tumor. The control animals were intraperitoneally or intratumorally injected with a physiological solution or underwent a corresponding operational trauma.

The antitumor activity of the test compounds was assessed for the following biological characteristics; the degree of inhibition of the tumor growth, survival of animals on the 10th day after inoculation of the tumor cells, life span of the animals.

The tests showed that upon intraperitoneal and superselective intratumoral administration of the test compounds similar biological characteristcs were obtained. The results of the tests are shown in Table 1 hereinbelow.

As it is seen from Table 1, free polymethylsiloxane does not inhibit the tumor growth, neither it lower the life span of the tumor carriers, does not affect their survival.

The compounds according to the present invention are not inferior to CDDP or even superior over it in characteristics of the antitumor activity. Especially advantageous is the compound II which is more active than CDDP in inhibition of the tumor growth, increases survival of the animals by 20% and extends their life span by 10 days, i.e. two times.

The compounds according to the present invention were tested for an acute toxicity. An acute toxicity of the compounds I, II and III according to the present invention was studies in comparison with free CDDP and poloymethylxiloxane on white non-descript rats with a mass of 150-200 g and on white non-line mice with the mass of 30±3 g having passed quarantine of not shorter than 20 days and kept on a standard diet of a vivarium. The test animals were divided into groups of 10 species in each. The test substances were administered intraperitoneally for a single time. CDDP was injected in the form of an aqueous solution containing additionally 0.015 m of NaCl and 0.0015M of sodium citrate (pH = 7.0-7.2) in the volume of 3 ml in the doses of 8.0, 14.0, 16.0 and 18.0 mg/kg. Polymethylsiloxane and the compounds I, II and III according to the present invention were administered intraperitoneally in the form of sterile powders in the doses: for polymethylsiloxane and the compound I of the present invention —400, 800, 1,600, 2,400, 3,200, 4,000 and 4,800 mg/kg; for the compound II—in the doses of 200, 400, 800, 1,200, 1,600, 2,000 and 2,400 mg/kg, for the compound III—in the doses of 130, 260, 530, 800, 1,060 and 1,300 mg/kg. Polymethylsiloxane and the compounds I, II and III were introduced into an opened peritoneal cavity of the animals preliminarily narcotized with dexenal in a dose of from 40 to 60 mg/kg for rats, 20-30 mg/kg—for mice. After administration of the compounds the abdominal cavity was sewn by a purse-string stuture. The assessment of death rate of the animals was effected 24 and 48 hours after administration of the compounds. An acute toxicity of the compounds was expressed in the form of the doses causing perdition of 50% and 100% of the animals ($LD_{50}$ and $LD_{100}$).

TABLE 1

| Compounds | Degree of inhibition of the tumor growth, % | Survival of animals, % | Life span, days |
|---|---|---|---|
| CDDP | 78 | 80 | 11.5 ± 0.5 |
| Polymethylsiloxane | 0 | 100 | 14.5 ± 0.5 |
| Compound I of the present invention | 94 | 100 | 21.0 ± 0.5 |
| Compound II of the present invention | 95 | 100 | 21.5 ± 1.0 |
| Compound III of the present invention | 84 | 90 | 18.5 ± 1.0 |
| Control | 0 | 100 | 14.5 ± 0.5 |

The tests of an acute toxicity of the compounds according to the present invention on rats and mice gave similar results.

The compounds according to the present invention were assessed for a therapeutic efficiency by the therapeutic index (ratio of $LD_{50}$ to ED). The results of the determination of the acute toxicity and the therapeutic index are shown in Table 2 hereinbelow.

TABLE 2

| Character-istics | CDDP mg/kg | Poly-methyl-siloxane mg/kg | Compounds of the invention | | |
|---|---|---|---|---|---|
| | | | I mg/kg | II mg/kg | III mg/kg |
| 50 | 11.3 | >4,800 | 2,455 | 1,100 | 600 |
| 100 | 18.3 | >4,800 | 4,000 | 2,200 | 1,200 |
| Therapeutic index ($LD_{50}$/ED) | 1.7 | — | 4.8 | 6.1 | 4.0 |

It is seen from Table 2 that polymethylsiloxane having no therapeutic activity does nt provide any toxic effect even in a dose exceeding 4,800 mg/kg. The compounds according to the present invention are less toxic and more effective than CDDP. The less toxic out of them is the compound I. However, as regards the therapeutic effect, the most effective is the compound II according to the present invention.

The dead animals were subjected to an autopsy and morpholigical and histological investigations of the inner organs were performed. The animals administered with the compounds in doses lesser than the toxic one were slaughtered after 3, 7, 14 and 30 days. Their inner organs were also subjected to an autopsy.

According to morphological studies, polymethylsilxane and the compounds according to the present invention already on the 3rd day were fixed on the surface of the liver, spleen, intestine and other inner organs in the form of a deposit or small clumps coated on the outside by a transparent thin envelope. At the points of fixation of the administered compounds no macroscopic changes of the inner organs or the formation of commissures were found.

Histological investigations showed that upon administration of the compounds I, II and III according to the presen tinvention in doses lesser than the toxic one, the lungs, heart, intestine, brains ad stomach remained unchanged. Only a focal protein distrophy of the proximal small canals and individual renal glomeruli and an insignificantly pronounced distrophy of the liver tissue were observed. The causes of perdition of the animals administered with CDDP and the compounds I, II and III according to the present invention were the same in toxic doses. In this case there were observed pronounced distrophic changes of the inner organs, an acute nephroso-nephritis, massive necroses of glomeruli; edema of the stroma. In the intestine there was observed not-clearly pronounced dysplasia of epithelium and a reduced number of mitoses.

In the case of administration of the compounds I, II and III according to the present invention in doses lesser than the toxic one, the above-mentioned changes fully disappeared by the 14thd ay. In the case of administration of CDDP in similar doses the above-mentioned changes were pronounced to even greater extent than in the case of administration of the compounds according to the present invention, they were only partly restored on the 30th day after administration.

Histological investigations were also carried out on the intestine, liver and tumors of rats tumor-carriers which were administered with the compounds I and II according to the present invention. The tests were carried out on the 10th day after intraperitoneal and intratumoral administration of the compounds.

The test results are shown in Table 3 hereinbelow.

As it is seen from Table 3, the results of histological investigations show that the compound II according to the present invention more effectively destroys the tumor than the compound I, especially in the case of its intratumoral administration. The antitumor effect of the compound II is enhanced due to activation of the local reaction of the cell immunity, as well as due to the absence of local allergic and inflammatory reactions.

TABLE 3

| Compound I administered in the dose of 2,400 mg/kg | Compound II administered in the dose of 1,200 mg/kg |
|---|---|
| 1. Frequently encountered in the tissues are giant cells of a foreign body, up to 25-30 in the visible area which maintain the local inflammatory process. | 1. In the tissues the giant cells of a foreign body are substantially absent (1–3 in the visible area), local inflammatory response is absent. |
| 2. There are eosinophiles in tissues (up to 10 in the visual area) which points to the development of the local allergic reaction. | 2. No eosinophils in tissues, local allergic reaction is absent |
| 3. Lymphocytes in tissues are substantially not revealed which points to the absence of the local reaction of cellular immunity. | 3. An increased content of lymphocytes in tissues which points to activation of the local cell immunity enhancing destruction of tumor cells. |
| 4. In the case of intraperitoneal administration of the compound I there is observed a massive growth of a connecting tissue in the tumor among which isles of visible tumor cells are visible. | 4. In the case of intraperitoneal administration of the compound II there is observed in the tumor a massive growth of a connecting tissue among which isles of visible tumor cells are visible. |
| 5. When introduced directly into the tumor, in the zone of location of the compound I, among vast fields of necrosis of the tumor, there are foci of viable tumor cells. The adjacent regions of tissues are infiltrated with polymorpho-nucleous neutrophiles among which single eosinophiles are visible. | 5. When administered directly into the tumor, in the zone of location of the compound I a full destruction of the tumor is observed. In the adjacent regions necrobiosis and an intensive lymphocytic infiltration are observed. |

The immunological activity of the compound II according to the present invention was studied by variation of the characteristics of cellular and humoral immunity.

The effect of the compound II according to the present invention on the cell immunity was assessed by the time of rejection of a skin graft in the tumor-carriers. The effect on the humoral immunity was assessed by the number of antibody-forming cells in the spleen and antibodies in the blood serum formed in response to immunization, with ram ertyhrocytes, of both intact animals and the tumor-carriers.

The effect of the compound II according to the present invention on the cell immunity was studied on male rats of the Vistar line with a mass of 150–200 g. The animals were subjected to transplantation, by a standard method, of a skin graft of 2×3 cm size taken from rats of the August line. Then the animals were inoculated, under the thigh skin, with $2 \times 10^8$ cells of a regrafted strain of Schvetz's erythroleukosis. On the 4th day of the tumor development the animals were administered intraperitoneally with the compound II according to the present invention once in the dose equal to ½ of the $LD_{50}$ (550 mg/kg).

For the purpose of comparison use was made of CDDP and polymethylsiloxane which was administered in the doses of 5.6 and 2,000 mg/kg respectively. CDDP was administered in a solution, while polymethylsiloxane and the compound II of the present invention—as a powder which was introduced into an opened abdominal cavity following to above-described procedure. The intact animals were used as a control. The time of rejection of the skin graft was fixed by variation of its temperature, colour and elasticity. The results of the tests are shown in Table 4 hereinbelow.

TABLE 4

Time of Rejection (in days) of a Skin Graft in Intact Animals and Tumor-Carriers without Treatment and with the Treatment with the Compound II According to the Invention

| Intact animals | Tumor-carriers without treatment | Tumor-carriers with treatment using | | |
|---|---|---|---|---|
| | | CDDP | Poly-methyl-siloxane | Compound II of the invention |
| 9.5 ± 1.0 | 15.0 ± 1.0 | 13.5 ± 0.5 | 15.0 ± 1.0 | 14.5 ± 1.0 |

As compared to intact animals, in the non-treated tumor-carriers the time of rejection of the skin graft was extended by 5.5 days. This pointed to reduction of the cell immunity of the organisms under conditions of the tumor development. The introduction of CDDP, polymethylsiloxane and the compound II according to the present invention does not substantially affect the characteristics of the cell immunity of the tumor-carriers.

The effect of the compound II according to the present invention on the humoral immunity was studied also in comparison with CDDP and polymethylsiloxane. Use was made of rats of the Vistar line which were incoulated, under the thigh skin, with $2 \times 10^8$ cells of a regrafted strain of Schvetz'erthroleukosis. On the 4th day of the tumor growth CDDP was administered along with polymethylsiloxane and the compound II according to the present invention which were introduced by the same method as in the study of the cell immunity. On the 8th day after regrafting of the tumor the animals were subjected to immuniation by way of an intravenous administration of ram erythrocytes in the dose of $1 \times 10^6$ cells. 4 days after immunization the animals were slaughtered by decapitation against the background of ethereal narcosis, the spleen was taken out and the content of antobidy-forming cells was determined threein by Erne'method, as well as titres of ag-glutinines and hemolysines in the peripheral blood using known methods.

The content of antibody-forming cells was determined for $10^6$ splenocytes and for the entire mass of the spleen. The results of the tests are shown in Table 5 hereinbelow.

As it is seen from Table 5, CDDP inhibits the humoral immunity, whereas the compound II according to the present invention, likewise polymethylsiloxane, does not change the humoral immunity of the tumor-carrier. In contrast to CDDP it does not lower the number of antibody-forming cells in the spleen and the content of antibodies in teh blood serum, while staiblizing tehse parameters at the level characteristic for the non-treated animals.

The characteristics of the functional activity of the liver and kidneys of rats were also studied. The intact animals were administered with polymethylsiloxane intraperitoneally in the single dose of 2,000 mg/kg, as well as CDDP and the compound II according to the present invention in intermediate toxic doses equal to $\frac{1}{2}$ of the $LD_{50}$. All the test substances were administered in much the same way as in the determination of the acute toxicity.

TABLE 5

| | | Groups of animals | |
|---|---|---|---|
| No. | Humoral immunity characteristics | Intact animals | Tumor-carriers without treatment |
| 1. | Content of antibody-forming cells per $10^6$ of splenocytes | 2,530 ± 550 | 285.7 ± 22.7 |
| 2. | Content of antibody-forming cells for the entire spleen | (1,828 ± 230) × $10^3$ | (250.5 ± 20.3) × $10^3$ |
| 3. | Titre of agglutinines | 1:625 | 1:256 |
| 4. | Titre of hemolysines | 1:4,064 | 1:2,256 |

| | | Groups of animals tumor-carriers administered with | |
|---|---|---|---|
| No. | CDDP | Xerogel of polymethyl-siloxane | Compound II of the invention |
| 1. | 20.50 ± 2.15 | 297.4 ± 21.98 | 257.4 ± 15.3 |
| 2. | (36.42 ± 2.15) × $10^3$ | (276.15 ± 14.02) × $10^3$ | (300.0 ± 20.42) × $10^3$ |
| 3. | 1:64 | 1:256 | 1:256 |
| 4. | 1:128 | 1:2,048 | 1:2,050 |

24 hours and 7 days thereafter the animals were slaughtered and certain biochemical characteristics of the blood illustrating the functional state of the liver and kidneys were determined. The results of the tests showed that during the first day after administration of CDDP in the dose equal to $\frac{1}{2}$ of the $LD_{50}$ there was noticed a statistically certain increase of the activity of transaminases (alanineaminotransferase and aspartateaminotransferase), the level of bilirubin and an increase of the amount of uric acid in the blood serum. On the 7th day after administration of CDDP these characteristics remained higher than the normal ones. The obtained results demonstrated that no normalization of the parameters of the functional activity of the liver and kidneys in the animals administered with CDDP occurred by the 7th day. Upon administration of polymethylsiloxane and of the compound II according to the present invention no statistically certain changes in the parameters of the functional activity of the liver and kidneys were noticed within the short period (24 hours) or within a longer period (7 days) after their administration.

The results of the carried out biochemical studies were supported by the data of histological investigations of the tissues of the liver and kidneys.

The complex of parameters revealed as a result of the carried out experiments: high values of the degree of inhibition of the tumor growth, survival of animals and their life span simultaneously with lowering of toxicity enabled administratino of the compound II according to the present invention as a pharamceutical agent for the treatment of malignant tumors.

An additional advantage of the compound II according to the present invention is the absence of immunodepressing properties therein, as well as promotion of the local cell immunity in zones of contact of the compound with tissues upon its administration which also ensures the possibility of its use in chemotherapy of malignant tumors.

The antitumor agent according to the present invention incorporating the active principle—the most active compound II according to the presen tinvention was subjected to clincal tests. The latter were carried out on 77 patients with ovary cancer of the IV clincial stage of Group IV aged 14 to 68 years. In all cases the diagnosis was justified by the results of histological studies.

Depending on the treatment method all the patients were divided into 2 groups.

In the first grup (30 patients) during non-radical operations in a maximum possible volume after resection of the tumor, direclty within the bed of the removed tumor, the compound II according to the present invention was applied onto the non-removed foci and adjacent tissues in the form of a sterile powder (sterilization by autoclaving) in a dose of2,500-3,000 mg per one patient with a bodymass of 50-75 kg ensuring a maximum possible uniform distribution of the powder. The post-operation period had no complications. 5-7 days after the operation intraperitoneal chemotherapy with CDDP was carried out.

In the second group (47 patients) only the intraperitoneal chemotherapy with CDDP was carried out.

During the period of therapy with he compound according to the presen tinvention the content of urea and creatinine in the blood serum and the content of protein in urina was not beyond the interval of physiologicla fluctutations.

The variation of the content of bilirubin and of the activity of transaminases in the blood was also within the range of physiological fluctuations.

The results of clinical studies of the biochemical characteristics are in agreement with the results of the studies carried out in experiments on animals; they point to the absence of both nephrotoxic effects of the compound according to the present invention.

Clincial and laboratory investigations of the characteristics of the cell and humoral immunities after the performed chemotherapy with the compound according to the present invention have shown the absence of immunodepressing properties therein. The content of T-, B-lymphocytes, immunoglobulins in the blood serum did not differ from similar characteristics in the patients with thes ame pathology to whom the compound according to the present invention was not administered during the operation.

Consequently, the compound according to the present invention provides no immunodepressant effect.

The comparison of the distant results of the treatment of the patients of the first and second grups showed that in group I a full remission was noticed in 15 patients (50%), a partial remission and stabilization of the process was noted in 14 persons (47%) 2-3.5 years after the operation. One female patient dies 1 year after the operation (3%).

In the second gruop of patients a full remission was noticed in 14 persons (30%), partial remission and stabilization of the process—in 14 persons (30%), recurrence of the tumor growth was noted in 10 persons (21%), 9 months-1 year after the operation—9 persons died (19%). The administration of the preparation according to the present invention to patients suffering from ovary cancer in the clincial stage IV during the operation by way of its direct application onto the tumor and tissues adjacent thereto, followed by an intraperitoneal chemotherapy with CDDP is more effective as compared to a similar chemotherapy wtihout a preliminary application of the compound according to the present invention. The use of the agent according to the present invention makes it possible to substantially improve the results of therapy of non-operable patients.

Therefore, the use of the agent according to the present invention ensures the possibility of chemotherapy by way of provision of a high concentration of the antitumor compound and its deposition of malignization foci at a minimum general toxic effect on the organism. As compared to other palliative methods of treatment of non-operable malignant ovary tumors administration of the preparation according to the present invention improves efficiency of a complex chemotherapy, makes it possible to ameliorate the state of patients and extend their life span.

The pharmaceutical agent according to the present invention has the following contraindications: it should not be administered in the case of a clearly pronounced renal insufficiency, strong dehydration and a substantial loss of blood.

The preparation according to the present invention should be preferably administered in the form of a sterile powder in a dose of 2,500-3,000 mg per a patient with a bodymass of 50-75 kg, introduced directly into the bed of a resected tumor, directly onto tumor foci which cannot be resected, onto the tissues adjacent to the tumor.

The compounds according to the present invention are prepared in the following manner. A complex compound of platinum (II) is dissolved in an aqueous soultion of sodium chloride and the resulting solution is reacted with a hydrogel of polymethylsiloxane, followed by isolation of the desired product.

As the complex compound of platnium (II) use is made of cis-chlorodiamminoplatinum or sodium tetrachloroplatinite which is subjected to a preliminary treatment. The treatment of sodium tetrachloroplatinite is carried out with ammonium acetate in the molar ratio of 1:4, respectively, at the boiling temperature with isolation of the formed precipitate. The hydrogel of polymethylsiloxane is obtained from an aqueo-alkaline solution of sodium methylsiliconate and hydrochloric acid following a known procedure (Slinyakova I. B., Denisova T. I. ''Organosilicon Adsorption'', 1988, Kiev, "Naukova Dumka" Publishers, pp. 25-28).

The compound (I) according to the present invention with a unit:

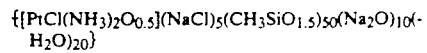

is obtained at the ratio Pt:si:NaCl equal to 1:50:23.

The compound (II) according to the present invention having a unit:

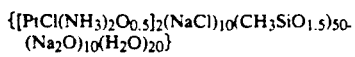

is prepared at the ratio of Pt:Si:NaCl equal to 2:50:46.

The compound (III) according to the present invention having a unit:

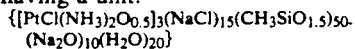

is prepared at the ratio of Pt:Si:NaCl equal to 3:50:69.

The desired product is recovered from the reaction mixture by drying in a current of air.

For a better understanding of the present invention, some specific examples of the preparation of the claimed compounds are given hereinbelow by way of illustration.

EXAMPLE 1

A solution of 4.5 g (75 mmol) of sodium chloride and 1.0 g (3.33 mmol) of cis-dichlorodiamminoplatinum in 500 ml of water were mixed with 500 ml of a hydrogel of polymethylsiloxane containing 50.0 g of the active principle which, as calculated for silicon, was equal to 166.5 mmol. The resultign mixture was dried in a current of air till the formation of a xerogel in the form of a bulky powder-like substance. There were thus obtained 50.0 g (90%) of a polymer having a unit:

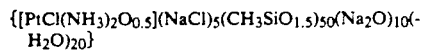

in the form of a fine white powder with a yellowish shade, with a globule diameter of 4.0-7.0 nm, a specific surface area of $S=80-200$ m$^2$/g and with the following parameters of a UV-spectrum of a subpension containing 0.048 g of the compound in 10 ml of glycerol: $\lambda_{max}=215.5$ nm, $\lambda_{max}=95.5$ nm, $E_{215.1}^{1\ cm}=0.240$, $E_{295.5}^{1\ cm}=0.045$.

Found; %: Pt 3.99, Cl 4.28, C 12.37, N 0.54, H 4.20, Si 28.62, Na 11.98. $C_{50}H_{196}O_{105.5}Na_{25}N_2Cl_6PtSi_{50}$.

Calculated, %: Pt 3.99, Cl 4.36, C 12.27, N 0.57, H 4.01, Si 28.65, Na 11.77.

EXAMPLE 2

The process was carried out in a manner similar to that described in the foregoing Example 1, except that instead of ci-dichlorodiamminoplatinum use was made of 1.31 g of sodium tetrachloroplatinite treated with 1.10 g of ammonium acetate at the boiling temperature with isolation of the formed precipitate. A product was thus obtained with a UV spectrum of its suspension at the content of b 0.048 g of the compound in 10 ml of glycerol having the following parameters: $\lambda_{max}=215.7$ nm, $\lambda_{max}=295.4$ nm, $E_{215.7}^{1\ cm}=0.235$, $E_{295.4}^{1\ cm}=0.040$. The resulting compound was idential, as regards its chemical composition, to the compound prepared in Example 1.

EXAMPLE 3

The process was carried out in a manner similar to that of Example 1 hereinbefore, except aht the hydrogel of polymethylsiloxane was used in the amount of 250 ml which contained 25.0 g of the main substance (83.3 mmol as calculated for elemental silicone). There were obtained 25.0 g (93%) of a polymer having a unit:

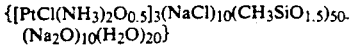

in the fomr of a fine white powder with a yellowish shade, with a globule diameter of 4.0-7.0 nm and with a specific surface area of 80-100 m$^2$/g and with the following parameters of a UV-spectrum of a suspension prepared from 0.047 g of the compound in 10 ml of glycerol: $\lambda_{max}=217.9$ nm, $\lambda_{max}=278.5$ nm, $\lambda_{shoulder}=333.5$ nm, $E_{217.9}^{1\ cm}=0.490$, $E_{278.5}^{1\ cm}=0.080$. $E_{333.5}^{1\ cm}=0.035$.

Found, % Pt 7.01, Cl 7.92, C 11.28, N 1.12, H 3.52, Si 25.80, Na 12.80.

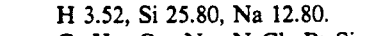

Calculated, %: Pt 7.14, Cl 7.80, C 10.98, N 1.02, H 3.70, Si 25.69, Na 12.63.

EXAMPLE 4

The process was carried out in a manner similar to that of Example 3 hereinabove, except that the complex compound of platinum was sodium tetrachloroplatinite treated with ammonium acetate and prepared as in Example 2. A product was thus obtained whose UV-spectrum of a suspension containing 0.047 g of the compound in 10 ml of glycerol had the sam eparameters as the product prepared in Example 3. The resulting product had the same chemical composition as the compound prepared in Example 3 hereinabove.

EXAMPLE 5

The process was carried out in a manner similar to that described in Example 1, except that the hydrogel of polymethylsiloxane was used in the amount of 127 ml which contained 16.7 g of the main substance (55.5 mmol as calculated for silicone). There were obtained 15.0 g of a polymer having a unit:

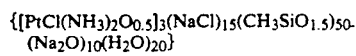

in the fomr of a white fine powder with a yellowish shade, with a globule diameter of 4.0-7.0 nm, with a specific surface area of 80-200 m$^2$/g, with the parameters of a UV-spectrum of a suspension prepared from 0.048 g of the compound in 10 ml of glycerol: $\lambda_{max}=219.1$ nm, $\lambda_{max}=270.5$ nm, $E_{219.1}^{1\ cm}=0.750$, $E_{270.5}^{1\ cm}=0.125$.

Found, % Pt 9.70, Cl 10.45, C 10.15, N 1.36, H 3.61, Si 23.21, Na 13.48.

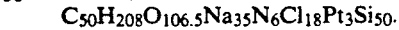

Calculated, %: Pt 7.71, Cl 10.61, C 9.96, N 1.39, H 3.45, Si 23.24, Na 13.36.

EXAMPLE 6

The process was carried out in a manenr similar to that described in Example 5, except that the complex compound of platnium was sodium tetracloroplatinite treated as described in Example 2 hereinbefore. The resulting product has its chemical composition and the UV spectrum (for a suspension) identical to the product obtained in the foregoing Example 5.

INDUSTRIAL APPLICABILITY

Compounds of the present invention derivatives of platinum (II) with polymethylsiloxane exhibit an antitumor activity and find application in medicine as an agent of an antitumor effect for administration directly onto the tumor and adjacent tissues in chemotherapy of ovary cancer, mammal carcinoma, pancreas carcinoma, gallbladder carcinoma, cancer of large and small intestine.

We claim:

1. Derivatives of platinum (II) with polymethylsiloxane comprising exerogels—a product of interaction of a omplex compound of platnium (II) in an aqueous solution of sodium chloride with a hydrogel of polymethylsiloxane at a molar ratio of Pt:Si:NaCl equal to 1-3:40:-23-69 representing a three-dimensionally cross-linked polymer of a globular structure with a globule diameter of form 4.0 to 7.0 nm and with a specific surface area of from 80 to 200 m²/g having a unit of the general formula:

$$\{[PtCl(NH_3)_2O_{0.5}]_n(NaCl)_{5n}(CH_3SiO_{1.5})_{50}(Na_2O)_{10}(H_2O)_{20}\}$$

wherein n is 1 to 3.

2. A method for preparating derivatives of platnium (II) with polymerhtylsiloxane according to claim 1, Characterized in that a complex compound of platinum (II) in a an aqueous solution o sodium chloride is reacted with a hydrogel of polymethylsiloxane at a molar ratio of Pt:Si:NaCl equal to 1-3:50:23-69, followed by isolation of the desired product.

3. A method according to claim 1, Characterized in that as the complex compound of platinum (II) cis-dichloroamminoplatinum is used.

4. A method according to claim 2, Characterized in that as the complex compound of platinum (II) sodium tetrachloroplatinite is used which prior to the reaction with the hydrogel of polymethylsiloxane is preliminarily treated in water with ammonium acetate in the molar ratio of 1:4, respectively, at the boiling temperature with separation of the formed precipitate.

5. An antitumor agent for administration directly onto the tumor and tissues adjacent thereto Characterized in that it consists of an active principle—a derivative of platinum (II) with polymethylsiloxane according to claim 1, having a unit of the formula:

$$\{[PtCl(NH_3)_2O_{0.5}]_2(NaCl)_{10}(CH_3SiO_{1.5})_{50}(Na_2O)_{10}(H_2O)_{20}\}$$

* * * * *